United States Patent [19]

Kogan

[11] Patent Number: 5,203,349
[45] Date of Patent: Apr. 20, 1993

[54] ELECTRICAL PULSE GENERATING DEVICE FOR THERAPEUTIC USES

[75] Inventor: Henry Kogan, Paris, France

[73] Assignee: Anatomia International S.A., Paris, France

[21] Appl. No.: 814,573

[22] Filed: Dec. 30, 1991

[51] Int. Cl.$^5$ ............................................. A61N 1/32
[52] U.S. Cl. ..................................... 128/800; 128/421
[58] Field of Search ................................. 128/800–801, 128/421, 783

[56] References Cited

U.S. PATENT DOCUMENTS

| | | | |
|---|---|---|---|
| 4,099,519 | 7/1978 | Warren | 128/741 |
| 4,719,922 | 1/1988 | Padjen et al. | 128/421 |
| 4,741,347 | 10/1988 | Robert et al. | 128/800 |
| 4,920,981 | 5/1990 | Derieux | 128/800 |
| 5,063,929 | 11/1991 | Bartelt et al. | 128/421 |

FOREIGN PATENT DOCUMENTS

| | | | |
|---|---|---|---|
| 2183158 | 7/1987 | United Kingdom | 128/800 |
| 8704068 | 7/1987 | World Int. Prop. O. | 128/800 |
| 9004997 | 5/1990 | World Int. Prop. O. | 128/800 |

Primary Examiner—Lee S. Cohen
Assistant Examiner—Jeffrey R. Jastrzab
Attorney, Agent, or Firm—Pollock, Vande Sande and Priddy

[57] ABSTRACT

An electrical pulse generating device for therapeutic uses comprises a body containing a piezoelectric type generator and a head having at least two electrodes, an actuating trigger for operating the piezoelectric type generator, and a motor-reducer unit and control lever operatively connected to the actuating trigger and having a settable operating rhythm.

11 Claims, 4 Drawing Sheets

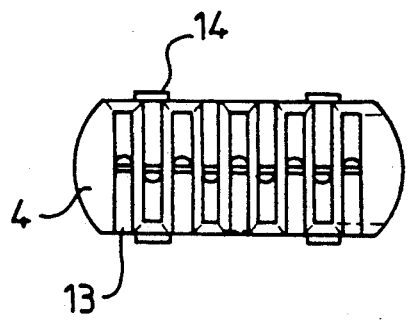
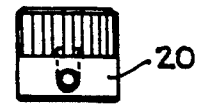
FIG. 4  FIG. 5
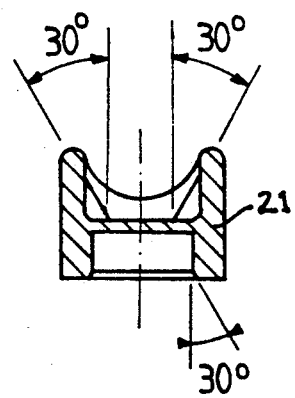
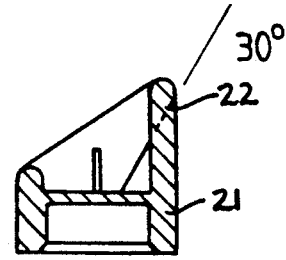
FIG. 6a  FIG. 6b

ELECTRICAL PULSE GENERATING DEVICE FOR THERAPEUTIC USES

The present invention relates to electrical pulse generating devices for therapeutic uses, which are used for various treatments in which it is useful that discharges and/or effluvia are brought to flow in some parts of the body of a patient.

BACKGROUND OF THE INVENTION

Devices for therapeutic uses are already known, in which a current of piezoelectrical origin is produced from a generator operated by hand. Such devices are used particularly for treatment of muscular pains, the current being led to flow between electrodes which are part of the device.

OBJECT AND SUMMARY OF THE INVENTION

The present invention has for its object a generating device of the above kind in which discharges and/or effluvia are produced by a piezoelectric type generator, while providing a better control of the frequency of the discharges and/or effluvia along the line of application thereof on the body of a patient as a function of the therapy applied.

According to the invention, the electrical pulse generating device for therapeutic uses comprises a body containing a piezoelectric type generator and a head having at least two electrodes respectively connected to terminals of the piezoelectric type generator, an actuating trigger for operating the piezoelectric type generator, means for controlling the actuating trigger, these control means being operatively connected to said actuating trigger and having a settable operating rhythm, whereby pulses are delivered across these at least two electrodes with a frequency which varies as a function of the operating rhythm.

Various other features of the invention will become more apparent from the following detailed description.

BRIEF DESCRIPTION OF THE DRAWINGS

Embodiments of the invention are shown, by way of non limiting examples, in the accompanying drawings, wherein:

FIG. 4 is a front view of the head of the device;

FIG. 5 is a front view of a mounting member of the device;

FIGS. 6a and 6b show details of an embodiment of a control cam of the device, as viewed along two cross sectional planes at 90° with respect to one another.

DESCRIPTION OF A PREFERRED EMBODIMENT

Figure 3B:
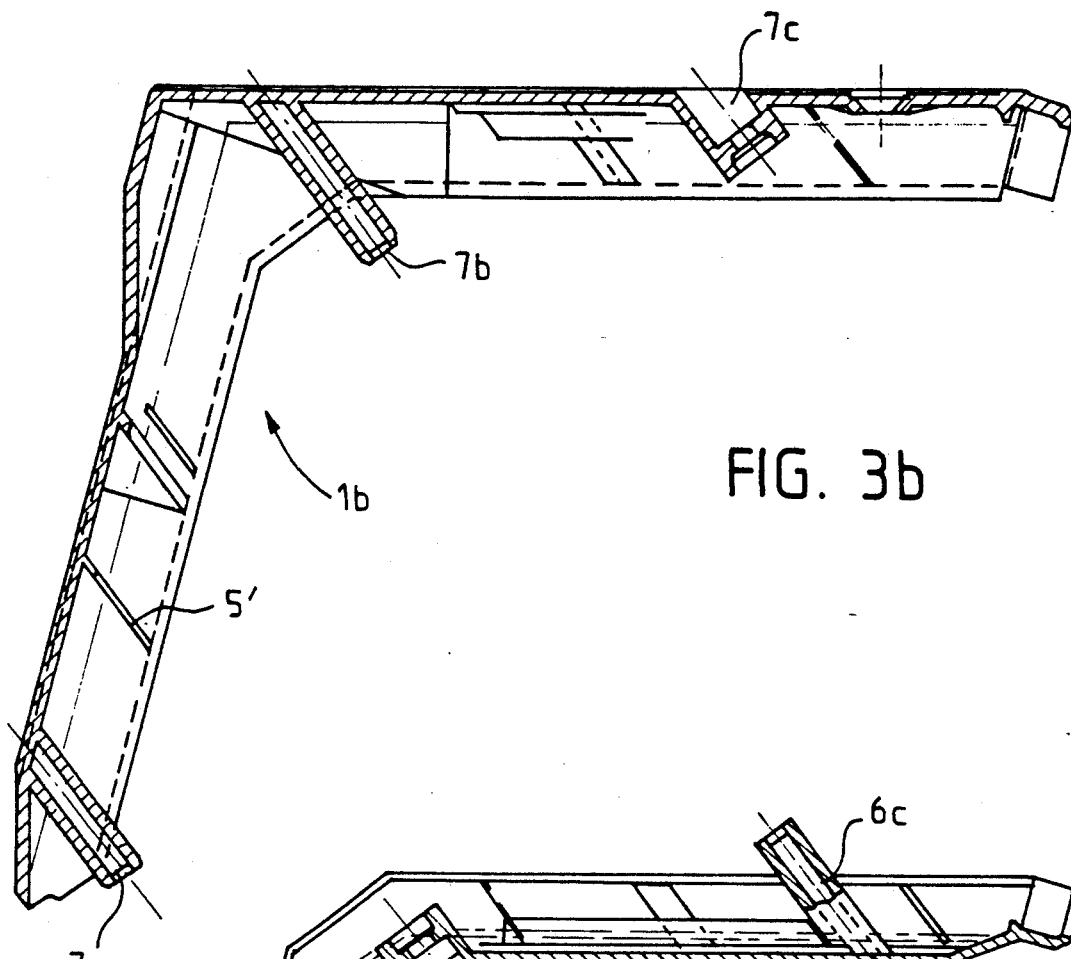
FIGS. 3a and 3b show a lower half-shell and an upper half-shell respectively, the assembly of which will form a body for the device.
Figure 3A:
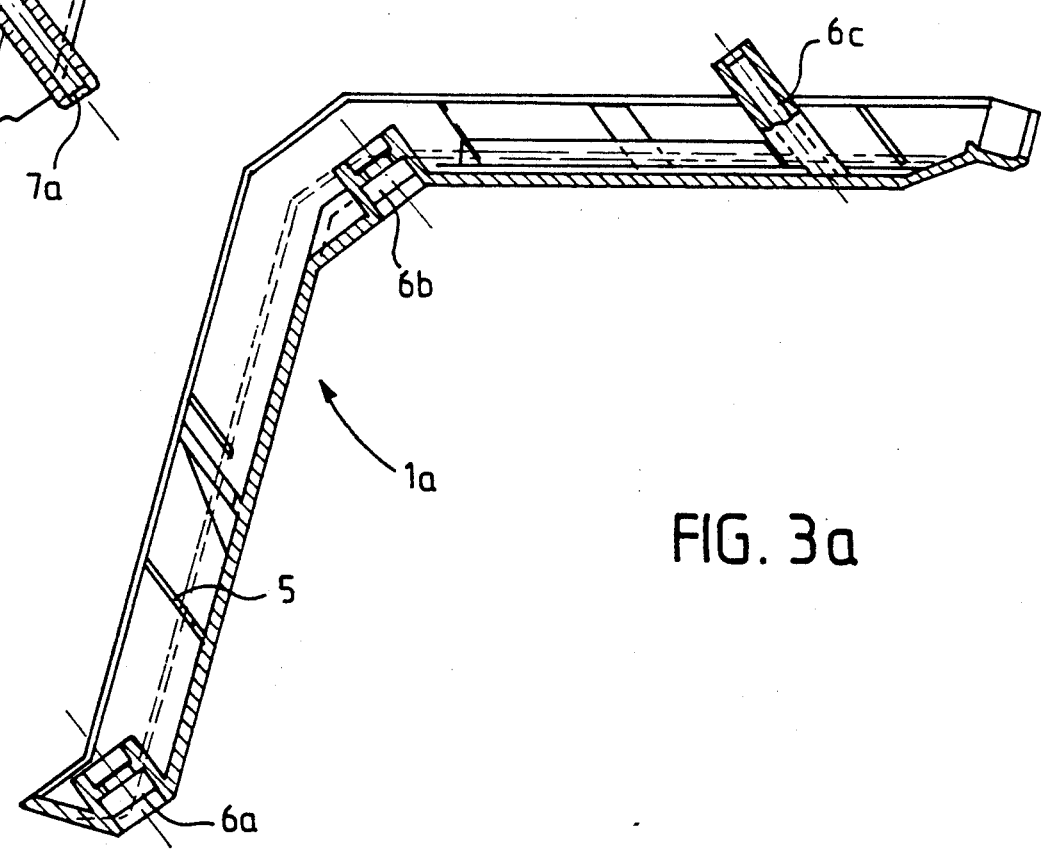

The device shown in the drawings comprises a body 1 of any shape, but which preferably has the shape of a gun made of two half-shells 1a and 1b, shown respectively in FIGS. 3a and 3b. The body 1 defines an arm 2 and a handle 3, the central axes of which form an angle preferably between about 100° and 110°. More preferably, this angle is substantially equal to 105° as shown.

Such an angular arrangement of the body 1 makes possible an easy holding in the hand, with assistance of the handle 3, by a person who has to apply a distributing head 4 (FIG. 4) on a portion of skin to be treated, this distributing head 4 being placed at a free end of the arm 2 of the body 1 of the device and inclined preferably at 15° with respect to the central axis of the arm 2.

As shown in FIG. 3a, the lower half-shell 1a is formed with a number of stiffening ribs, such as the rib 5, and contains housings 6a, 6b and 6c provided for cooperating with corresponding housings 7a, 7b and 7c in the upper half-shell 1b shown in FIG. 3b and which has also stiffening ribs 5'.

Figure 1:
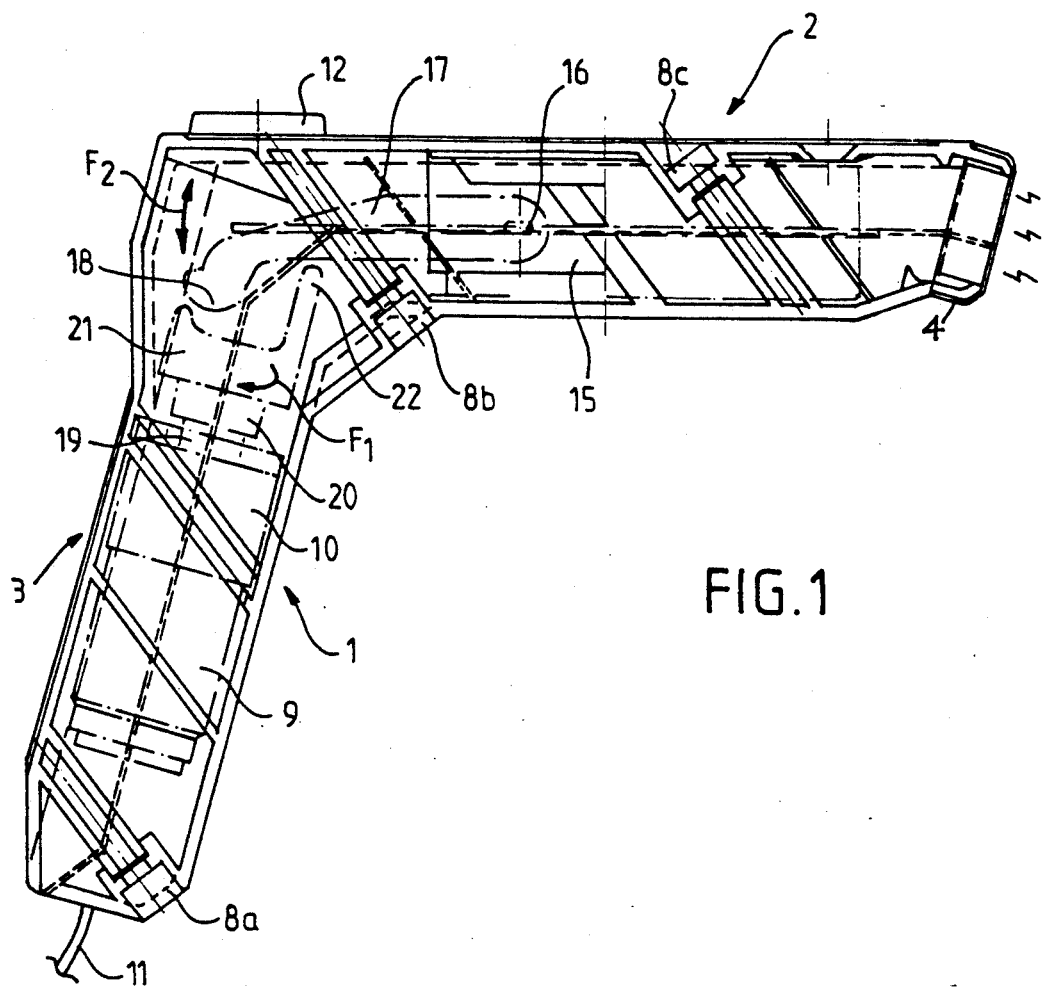
FIG. 1 is a partly broken-away view of the device of the invention which shows in phantom the active components of the device.

The two half-shells 1a and 1b are made so as to fit into one another. As shown in FIG. 1, screws 8a, 8b, 8c will rigidly interconnect the two half-shells 1a and 1b in order to form the body 1.

In FIG. 1, there is shown in phantom the active portion of the inventive device placed within the body 1.

Figure 7:
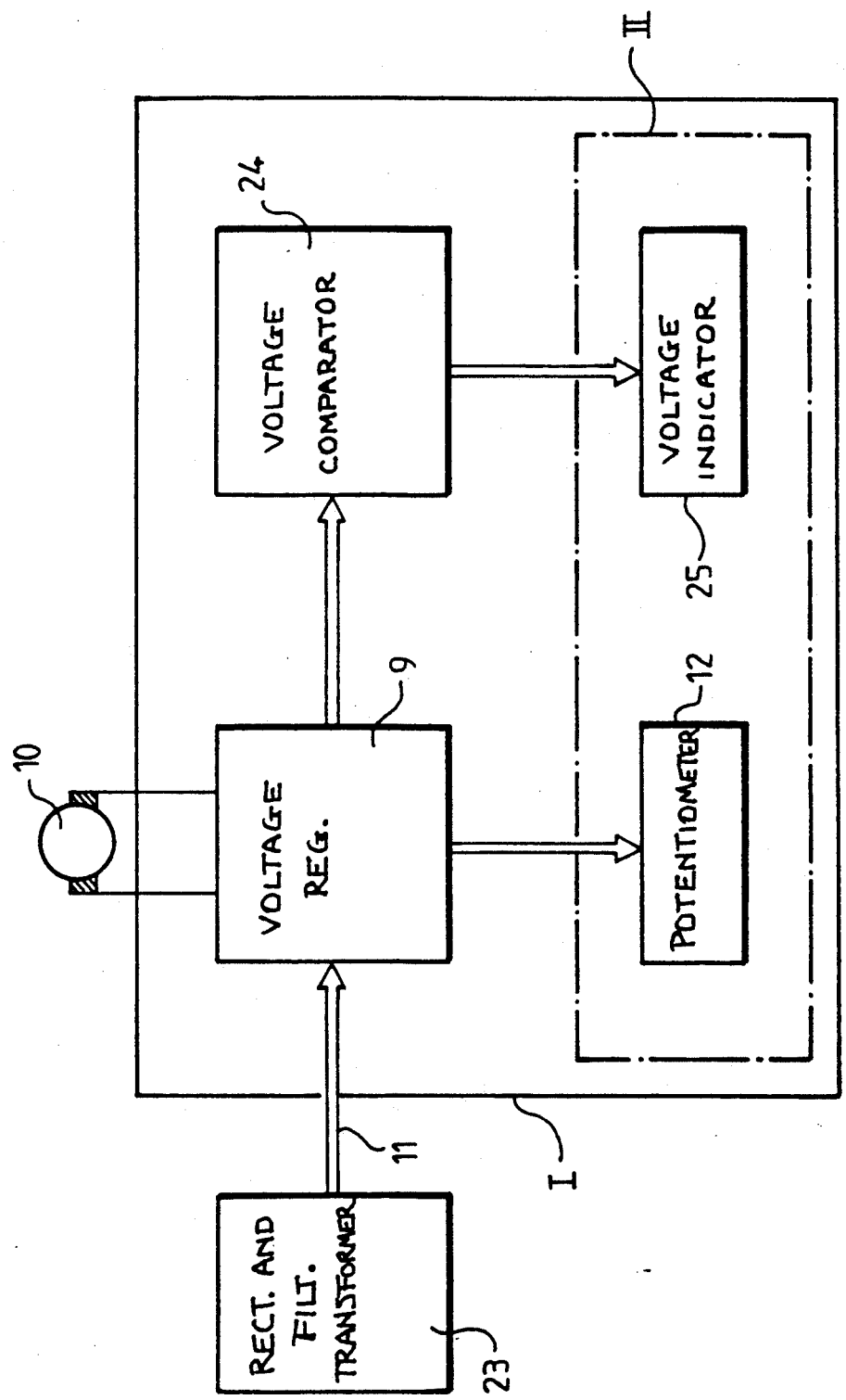
FIG. 7 is a block-diagram of the active components of the device.

A voltage regulator 9, the object of which will be better understood from explanations given further below in connection with FIG. 7, is provided for supplying a motor-reducer unit 10.

On an other hand, the voltage regulator 9 is connected by a wire 11, which thus extends outside the body 1 of the device, to a rectifying and filtering transformer so to form an adaptation block (not shown in FIG. 1) which is supplied for example by the network voltage. Such an adaptation block is well known in the art and there is no need to describe it in more detail, it being only noted that a rectified and filtered regulated voltage is obtained at output of the voltage regulator 9.

An adjusting potentiometer 12 having an ON/OFF switch is mounted on top of the body 1, and is connected to the voltage regulator 9 so as to vary the rectified and filtered regulator output voltage from the voltage regulator 9 which is applied to the motor-reducer unit 10.

As shown in FIG. 4, the distributing head 4 has, for example, a set of electrodes 13, 14, alternatively of even rank odd rank, and which are respectively connected across the terminals of a piezoelectric type generator 15 (FIG. 1) mounted in the arm 2, so that sparks can be formed between the even rank electrodes and the odd rank electrodes.

According to the invention, the piezoelectric type generator 15 has its actuating trigger, the end of which extends at 16 outside the generator, connected to a control lever 17 the free end 18 of which, of a rounded shape, is placed approximately at the meeting point of the central axes of the arm 2 and handle 3.

Likewise, the motor-reducer unit 10 has its output shaft 19 connected by a metallic insert 20 (see FIG. 5) to a cam 21 of plastics material, having a shape which is better shown in FIGS. 6a and 6b, and the upper portion 22 of which is also placed approximately at the meeting point of the central axes of the arm 2 and handle 3.

From the preceding disclosure, it is clear that a rotation of the motor reducer unit 10 will cause the cam 21 to rotate for example in a direction shown by the arrow $F_1$, and to drive the control lever 17 in a reciprocating alternate movement in a vertical plane as shown in FIG. 1 by the arrow $F_2$.

Thus, via its end 16, the trigger of the piezoelectric type generator 15 is actuated according to a rhythm which depends on the rotation speed of the motor-reducer unit 10, so that sparks will be delivered between the electrodes 13 and 14 of the head 4 with a frequency which is in turn a function of the speed of the motor-reducer unit 10.

In FIG. 7, which is a block-diagram of the device of the invention, the elements of the preceding figures are designated by the same reference numerals. FIG. 7 also shows a printed circuit diagrammatized by a rectangle in full line I, this circuit carrying the elements which are provided in the body 1 of the device; and, inside the full line rectangle I, a rectangle in phantom II shows the portion of the circuit which is visible above the body 1 of the device.

Figure 2:
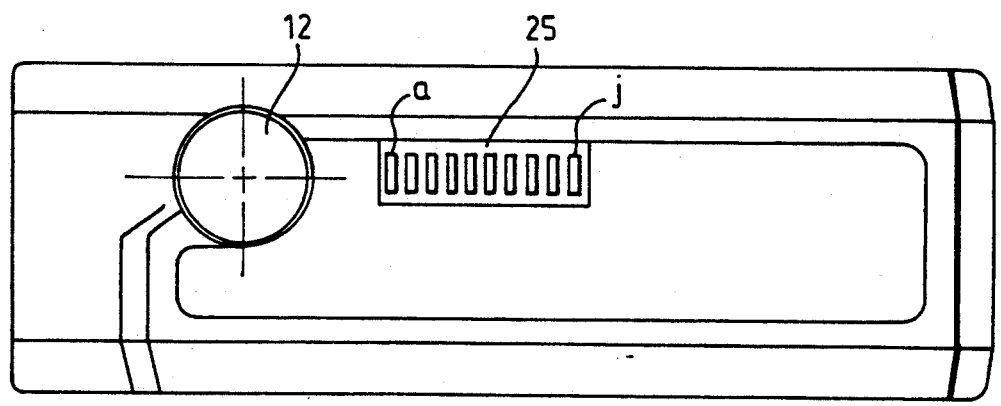
FIG. 2 is a top view of FIG. 1.

As shown in FIG. 7 and with reference to FIGS. 1 and 2, the rectifying and filtering transformer which has been previously discussed and which is designated here at 23 is connected to the voltage regulator 9, and the latter controls the motor-reducer unit 10 via the potentiometer 12.

The voltage regulator 9 is moreover connected, preferably via a voltage comparator 24, to a voltage indicator or display element 25 placed on the body 1 (see FIG. 2). The voltage display element 25 can be of any suitable type, and, in the preferred embodiment of the invention, the voltage display element 25 is a voltage indicator provided with light emitting diodes and called bargraph in the art. Such a voltage display element 25 is made of ten light emitting diodes (a . . . j), generally colored in red, the first diode of which is switched-on when the apparatus is started via the ON/OFF switch of the potentiometer 12, the various light emitting diodes being then switched-on thereafter in turn by steps of 1 volt upon operation of the potentiometer 12, while each time switching-off the preceding light emitting diode till the tenth light emitting diode j is switched-on indicating the maximum voltage applied by the voltage regulator 9 to the motor-reducer unit 10. Preferably, the potentiometer 12 is a linear type potentiometer, meaning that the voltage across its terminals will vary in a linear manner by a progressive operation of this potentiometer.

The voltage comparator 24 of FIG. 7 is a scale comparator of a known type having here a series of ten operating steps, and the voltage comparator 24 assesses the value of the output voltage of the regulator 9 applied as input to the motor-reducer unit 10, this voltage being made visible by the voltage display element 25.

It is thus clear that, as a function of the voltage applied to the motor-reducer unit 10, which voltage in the preferred embodiment of the invention can vary from 12 to 22 Volts according to the position given by the operator to the linear potentiometer 12, and which voltage is shown by the voltage display element 25, it is possible to smoothly control in a regular manner the rotation of the motor-reducer unit 10 (which rotation is thus carried out without reducing the torque applied to the control lever 17 of the piezoelectric type generator 15 via the cam 18), in order to smoothly vary in a regular manner the frequency of the voltage of piezoelectrical origin coming from the piezoelectric type generator 15 and applied between the electrodes 13 and 14 of the head 4. The frequency of the discharges and/or effluvia transmitted along their line of application on the body of a patient can easily be controlled as a function of the therapy applied.

The invention is not restricted to the embodiments shown and described in detail and various modifications thereof can be carried out thereto without departing from the scope of the invention as shown in the accompanying claims.

What is claimed is:

1. An electrical pulse generating device for therapeutic uses, comprising a body containing a piezoelectric type generator and a head having at least two electrodes respectively connected to terminals of said piezoelectric type generator, an actuating trigger for operating said piezoelectric type generator, motor means for controlling said actuating trigger, said motor means being operatively connected to said actuating trigger and having a settable operating rhythm, whereby pulses are delivered across said at least two electrodes with a frequency which varies as a function of said operating rhythm.

2. The device as set forth in claim 1, wherein said motor means includes a motor-reducer unit that is electrically connected to a voltage regulator controlled by a potentiometer.

3. The device as set forth in claim 2, wherein a voltage display element is mounted across said voltage regulator.

4. The device as set forth in claim 3, wherein a voltage comparator is operatively connected between the display element and the voltage regulator.

5. The device as set forth in claim 3 wherein said voltage display element is a light emitting diode indicator.

6. The device as set forth in claim 2, wherein said motor-reducer unit has an output shaft provided with a cam, said motor means also having a lever, said cam acting on said lever to displace said lever in a reciprocating alternate movement.

7. The device as set forth in claim 6, wherein said body is made of two half-shells fitted into one another, said body defining a handle and an arm, said head being mounted at one end of said arm, a central axis of said handle and a central axis of said arm forming an angle between about 100° and 110°, and one end of said lever being placed substantially at an intersection of said two central axes.

8. The device as set forth in claim 7, wherein said angle is substantially equal to 105°.

9. The device as set forth in claim 7, wherein said head is inclined at about 15° with respect to said central axis of said arm.

10. The device as set forth in claim 2, wherein said voltage regulator is supplied in current by a network voltage via a rectifying and filtering transformer.

11. The device as set forth in claim 2, wherein said potentiometer is a linear type potentiometer.

* * * * *